US012751961B2

(12) United States Patent
Kim et al.

(10) Patent No.: US 12,751,961 B2

(45) Date of Patent: Oct. 6, 2026

(54) COMPOSITION FOR PREVENTION, AMELIORATION, OR TREATMENT OF HYPERSENSITIVITY IMMUNE DISEASE CONTAINING GALACTOSE

(71) Applicant: Quorum Bio Co., Ltd., Seoul (KR)

(72) Inventors: Hye Eun Kim, Seoul (KR); Eunju Ryu, Seoul (KR); Jae Hyun Sim, Seoul (KR); Jun Sim, Incheon (KR)

(73) Assignee: QUORUM BIO CO., LTD., Seoul (KR)

( * ) Notice: Subject to any disclaimer, the term of this patent is extended or adjusted under 35 U.S.C. 154(b) by 588 days.

(21) Appl. No.: 18/031,670

(22) PCT Filed: Jul. 20, 2021

(86) PCT No.: PCT/KR2021/009326

§ 371 (c)(1),
(2) Date: Apr. 13, 2023

(87) PCT Pub. No.: WO2022/092495

PCT Pub. Date: May 5, 2022

(65) Prior Publication Data

US 2023/0381210 A1 Nov. 30, 2023

(30) Foreign Application Priority Data

Oct. 27, 2020 (KR) ........................ 10-2020-0140404

(51) Int. Cl.
*A61K 31/7004* (2006.01)
*A61P 17/00* (2006.01)
*A61P 37/08* (2006.01)

(52) U.S. Cl.
CPC .......... *A61K 31/7004* (2013.01); *A61P 17/00* (2018.01); *A61P 37/08* (2018.01)

(58) Field of Classification Search
None
See application file for complete search history.

(56) References Cited

U.S. PATENT DOCUMENTS

| | | | | |
|---|---|---|---|---|
| 2009/0131510 A1* | 5/2009 | Olsson | .................... | A61P 17/00 549/458 |
| 2023/0220327 A1* | 7/2023 | Duboux | ................. | C07K 14/81 435/252.1 |

FOREIGN PATENT DOCUMENTS

| | | | |
|---|---|---|---|
| CN | 102812049 | 12/2012 | |
| CN | 111165812 | 5/2020 | |
| JP | H07-330577 | 12/1995 | |
| JP | H09-227382 | 9/1997 | |
| JP | 2000-109419 | 4/2000 | |
| JP | 2022-538561 | 9/2022 | |
| KR | 10-0793912 | 1/2008 | |
| KR | 10-2013-0038845 | 4/2013 | |
| KR | 10-2017-0111281 | 10/2017 | |
| KR | 10-2018-0092911 | 8/2018 | |
| TW | 200927165 A * | 7/2009 | ............. A23C 9/127 |
| WO | 2007-116013 | 10/2007 | |
| WO | 2021-001367 | 1/2021 | |

OTHER PUBLICATIONS

Petrut, S., Rusu, E., Tudorache, I. S., Pelinescu, D., Sarbu, I., Stoica, I., & Vassu, T. (2019). Influence of various carbon sources on growth and biomass accumulation of some lactic acid bacteria strains. pharmaceuticals, 4, 5. (Year: 2019).*
Soichi Tanabe and Satomi Hochi, "Oral administration of a galactooligosaccharide preparation inhibits development of atopic dermatitis-like skin lesions in NC/Nga mice", International Journal of Molecular Medicine 25: 331-336, 2010, Mar. 1, 2010.
Editor-in-Chief: Jiang Xirui et al., "Biological fermentation Industry Technology; Technology of Biotech Fermentation Industry", China Light Industry Press, May 2016, p. 322, total 6pages.
SIPO, Office Action of the corresponding Chinese Patent Application No. 202180073608.5., dated May 16, 2025, total 10 pages.
JPO, Office Action of the corresponding Japanese Patent Application No. 2023-524411., dated Apr. 2, 2024, total 10 pages.
KIPO, PCT Search Report & Written Opinion of PCT/KR2021/009326 dated Nov. 1, 2021.
EPO, Extended European Search Report of the corresponding EP Patent Application No. 21886494.0, dated Aug. 6, 2024, total 7 pages.
JPO, Notice of Allowance of the corresponding Japanese Patent Application No. 2023-524411, dated Aug. 27, 2024, total 5 pages.
Kimiyuki Kaneko et al., "Development of hypoallergenic galacto-oligosaccharides on the basis of allergen analysis", Bioscience, Biotechnology, and Biochemistry, vol. 78, Issue 1, Jan. 2, 2014, pp. 100-108, https://doi.org/10.1080/09168451.2014.877819.

* cited by examiner

*Primary Examiner* — Dale R Miller
(74) *Attorney, Agent, or Firm* — LEX IP MEISTER, PLLC

(57) ABSTRACT

The present invention relates to use for the prevention and/or alleviation and/or treatment of hypersensitivity immune disease, containing galactose and, more particularly, provides a pharmaceutical composition and a health functional food that comprise galactose for the prevention, amelioration and/or treatment of hypersensitivity immune disease such as atopic dermatitis.

4 Claims, 5 Drawing Sheets

【FIG. 1】
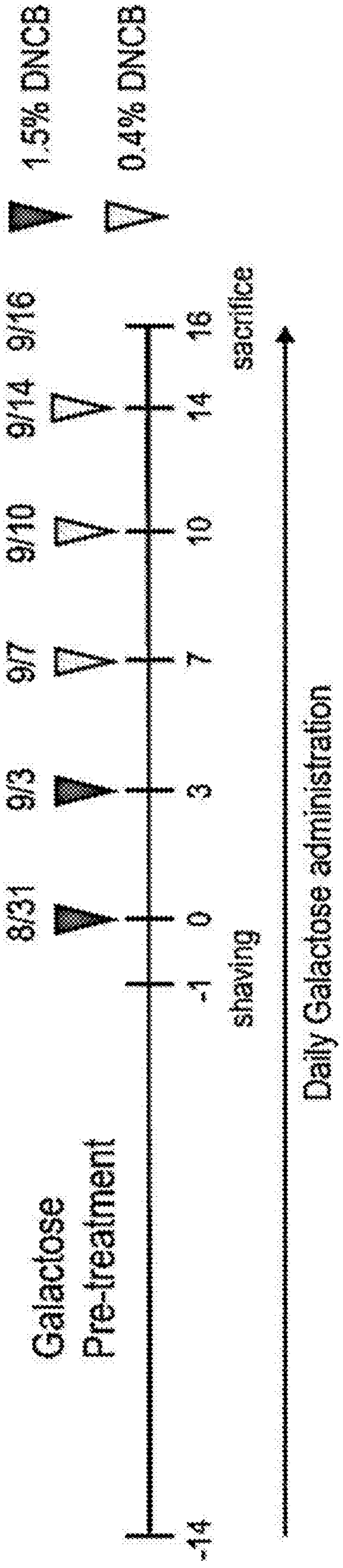

【FIG. 2】
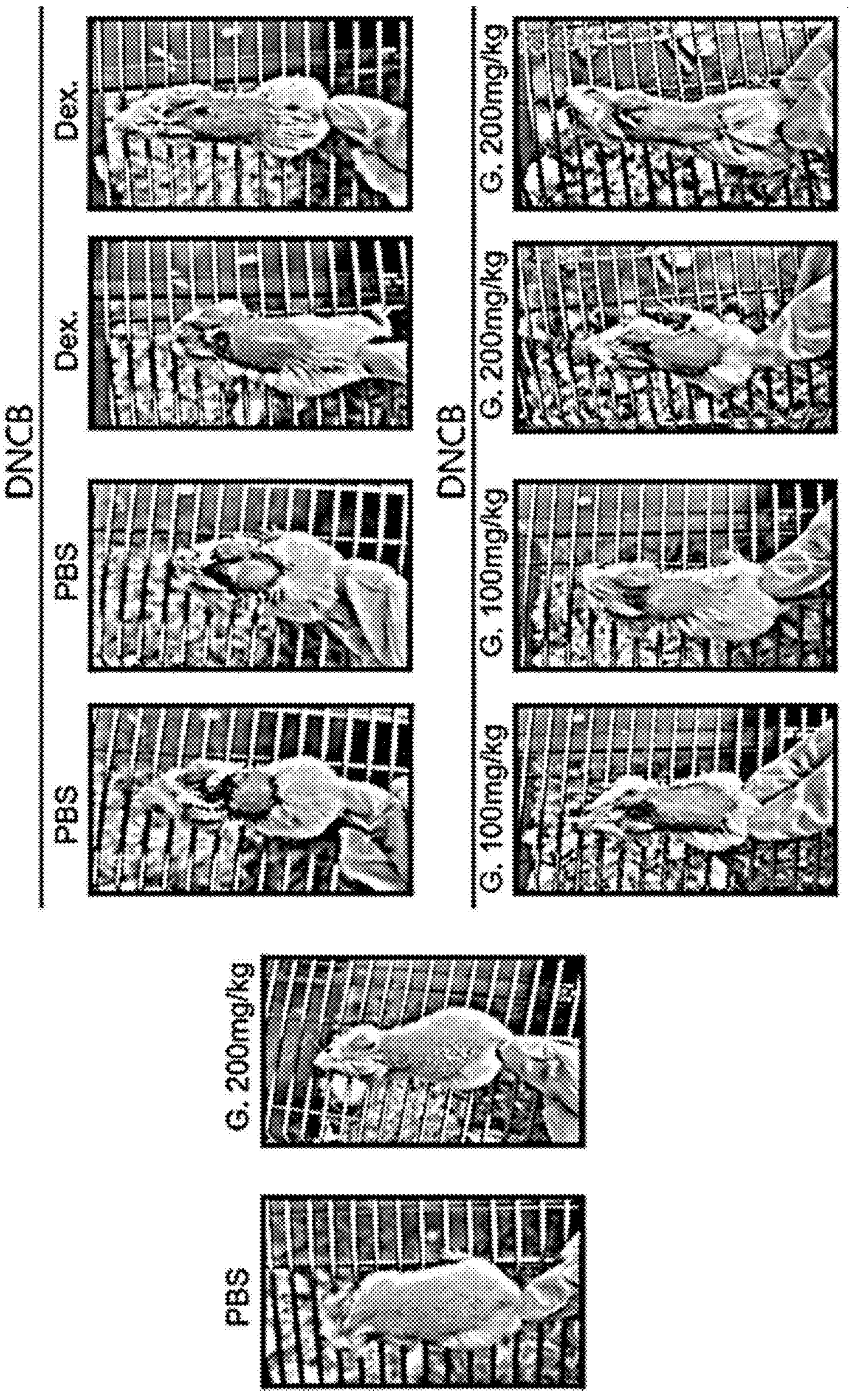

【FIG. 3】
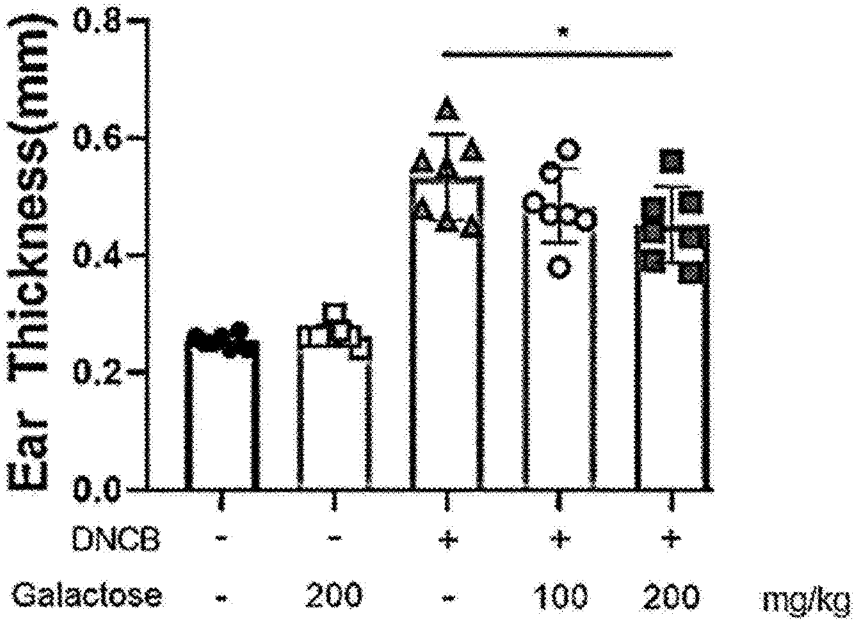
【FIG. 4】
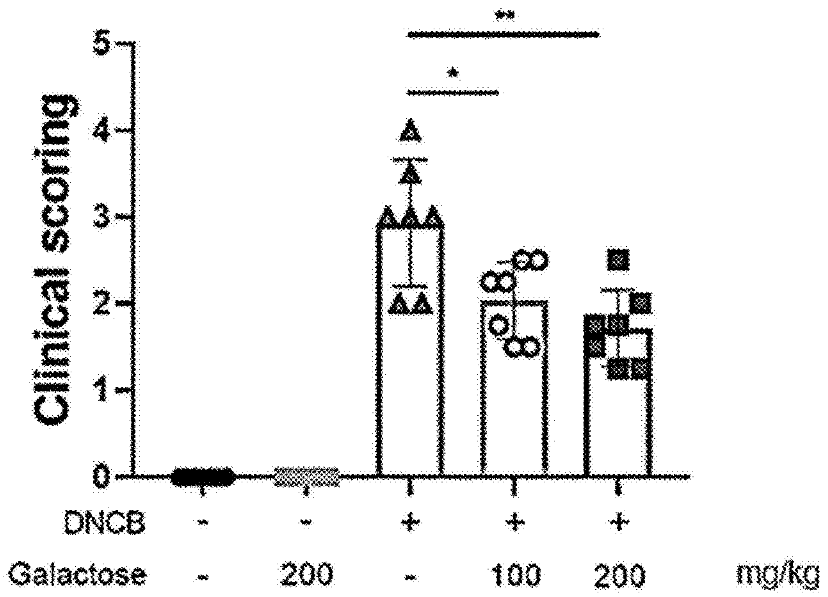

【FIG. 5】
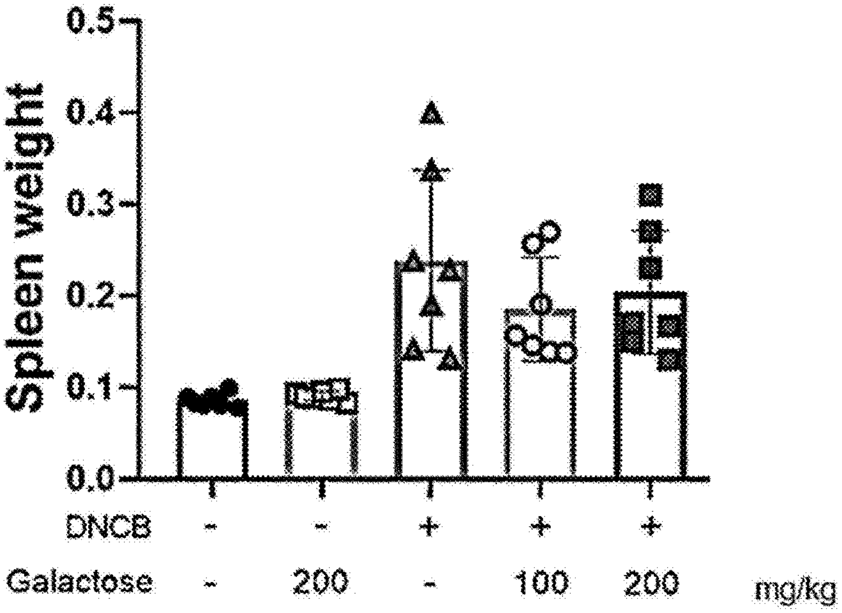
【FIG. 6】
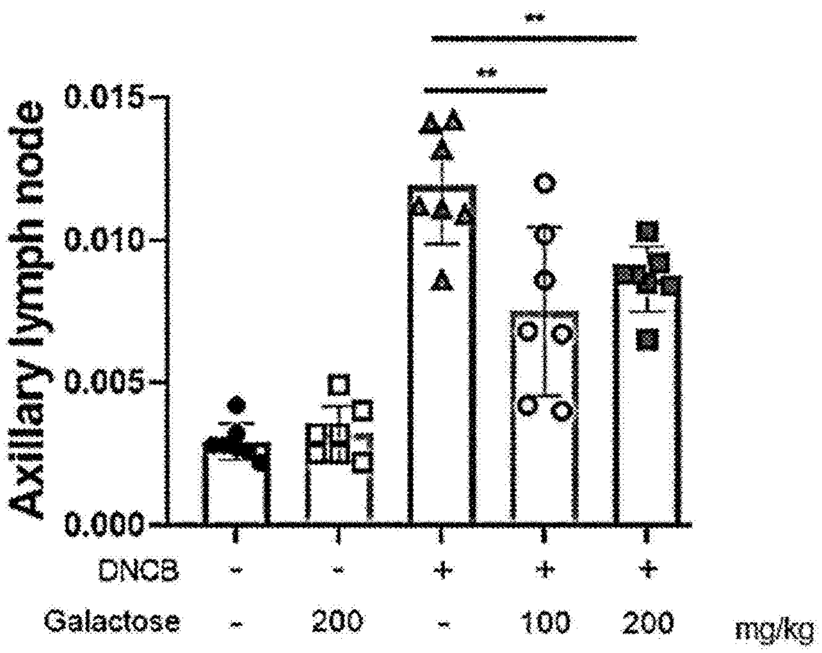

【FIG. 7】
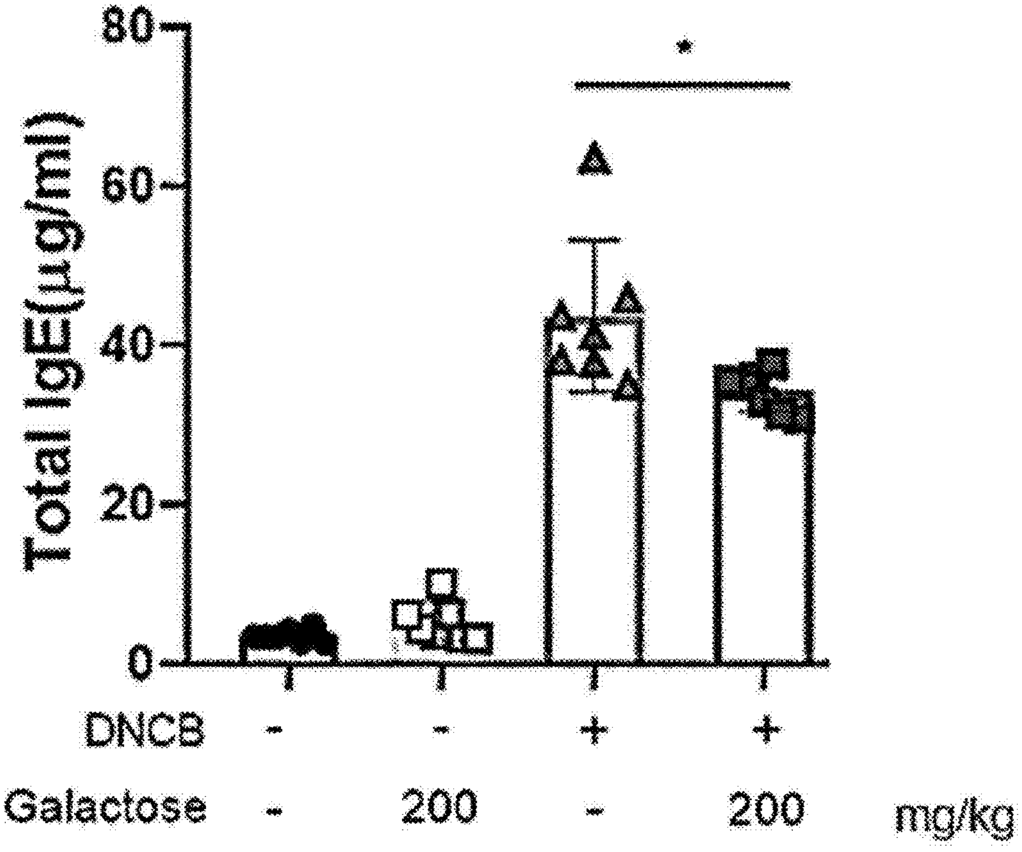

COMPOSITION FOR PREVENTION, AMELIORATION, OR TREATMENT OF HYPERSENSITIVITY IMMUNE DISEASE CONTAINING GALACTOSE

TECHNICAL FIELD

The present invention relates to uses for prevention and/or alleviation and/or treatment of immune hypersensitivity-related diseases containing galactose, and in particular, provides a pharmaceutical composition and a health functional food for prevention, alleviation and/or treatment of immune hypersensitivity-related diseases such as atopic dermatitis and the like comprising galactose.

BACKGROUND ART

Atopic dermatitis is one of the incurable diseases of modern people in the 21st century. It is a chronic, recurrent disease that usually begins in childhood and is accompanied by severe itching. According to the data of Korea Centers for Disease Control and Prevention, atopic dermatitis is a trend that is continuously increasing, and the prevalence rate is high, especially in children and adolescents, and the possibility of transition to adulthood is high. The current treatment strategy for atopic dermatitis prioritises moisturizing management and, in the event of an exacerbation, the temporary use of a topical anti-inflammatory drug is common. However, some patients complain of severe itching, and extensive skin lesions appear, and side-effects have been reported with continuous use of anti-inflammatory agents.

Antihistamines, steroids (cortisol, prednisolone, methylprednisolone, dexamethasone injections and ointments, etc.), moisturizers, etc. are generally used to treat atopic dermatitis, but they are not effective. In particular, in case of steroids, capillaries are dilated and the skin layer is thinned, resulting in a more severe hypersensitivity reaction, and moreover, when the steroids are stopped, a more severe symptom called steroid rebound is shown.

Therefore, there is a need to develop an effective therapeutic agent with low side effects for inflammatory skin diseases such as atopic dermatitis.

DISCLOSURE

Technical Problem

In the present description, uses for reducing immunoglobulin E and uses for prevention and/or treatment and/or alleviation of immune hypersensitivity-related disease of galactose are provided.

One embodiment provides a pharmaceutical composition for prevention and/or treatment of immune hypersensitivity-related disease comprising galactose. The pharmaceutical composition is for oral administration.

Another embodiment provides a health functional food for prevention and/or alleviation of immune hypersensitivity-related disease comprising galactose.

Another embodiment provides a cosmetic composition for prevention and/or alleviation of immune hypersensitivity-related disease comprising galactose.

Another embodiment provides a method for prevention and/or treatment of immune hypersensitivity-related disease, comprising administering galactose to a subject in need of prevention and/or treatment of immune hypersensitivity-related disease. The method may further comprise identifying a subject in need of prevention and/or treatment of immune hypersensitivity-related disease prior to the administration.

Another embodiment provides a use of galactose for using in prevention, treatment and/or alleviation of immune hypersensitivity-related diseases, or a use of galactose for using in preparation of a pharmaceutical composition, a health functional food and/or a cosmetic composition for prevention, treatment and/or alleviation of immune hypersensitivity-related disease, of galactose.

Another embodiment provides a composition for reducing immunoglobulin E comprising galactose. The composition may be in a form for oral administration. The composition may be used as a pharmaceutical composition, a health functional food, or a cosmetic composition. Another embodiment provides a method for reducing immunoglobulin E, comprising administering galactose to a subject in need of reducing immunoglobulin E. The method, may further comprise identifying a subject in need of reducing immunoglobulin E prior to the administration.

Another embodiment provides a use for using in reducing immunoglobulin E or a use for using in preparation of a pharmaceutical composition, a health functional food, and/or a cosmetic composition for reducing immunoglobulin E, of galactose.

Technical Solution

The present description confirms effects of treating/alleviating atopic dermatitis, reducing spleen and lymph nodes, and reducing immunoglobulin E, thereby suggesting uses for prevention and/or treatment and/or alleviation of immune hypersensitivity-related diseases.

One embodiment provides a pharmaceutical composition for prevention and/or treatment of immune hypersensitivity-related disease comprising galactose as an active ingredient. The pharmaceutical composition may be for oral administration.

Another embodiment provides a health functional food for prevention and/or alleviation of immune hypersensitivity-related disease comprising galactose as an active ingredient.

Another embodiment provides a cosmetic composition for prevention and/or alleviation of immune hypersensitivity-related disease comprising galactose as an active ingredient.

Another embodiment provides a method for prevention and/or treatment of immune hypersensitivity-related disease, comprising administering a pharmaceutically effective amount of galactose to a subject in need of prevention and/or treatment of immune hypersensitivity-related disease. The method, may further comprise identifying a subject in need of prevention and/or treatment of immune hypersensitivity-related disease prior to the administration.

Another embodiment provides a use for using in prevention, treatment and/or alleviation of immune hypersensitivity-related disease of galactose, or a use for using in preparation of a pharmaceutical composition, a health functional food and/or a cosmetic composition for prevention, treatment and/or alleviation of immune hypersensitivity-related disease.

Another embodiment provides a composition for reducing immunoglobulin E comprising galactose as an active ingredient. The composition may be in a form for oral administration. The composition may be used as a pharmaceutical composition, a health functional food, or a cosmetic composition. Another embodiment provides a method of reducing immunoglobulin E, comprising administering a pharmaceutically effective amount of galactose to a subject in need of reducing immunoglobulin E. The method, may further comprise identifying a subject in need of reducing immunoglobulin E, before the administering.

Another embodiment provides a use for using in reducing immunoglobulin E or a use for using in preparation of a pharmaceutical composition, a health functional food, and/or a cosmetic composition for reducing immunoglobulin E of galactose.

In the present description, the 'immune hypersensitivity-related disease' means disease caused by an excessive immune response to an antigen, and it may include a disease caused by a humoral immune hypersensitivity involved by immunoglobulin, for example, immunoglobulin E and/or a response related to cell-mediated immune hypersensitivity involved by T lymphocytes and macrophages, for example, various types of hypersensitivity, autoimmune disease, and the like. In one embodiment, the immune hypersensitivity-related disease may be hypersensitivity related to immunoglobulin E, enlarged spleen, enlarged lymph node, or disease related thereto. For example, the immune hypersensitivity-related disease may be at least one selected from the group consisting of atopic syndrome (e.g., atopic dermatitis, allergic conjunctivitis, allergic rhinitis, asthma, etc.), various types of allergy (e.g., allergic dermatitis), anaphylaxis, high-immunoglobulin E syndrome, autoimmune disease (e.g., systemic erythematosus lupus, rheumatoid arthritis, psoriasis, etc.), enlarged spleen, enlarged lymph node, and the like, but not limited thereto. In a specific embodiment, the immune hypersensitivity-related disease may be atopic dermatitis, allergic dermatitis (skin hypersensitivity reaction upon exposure to allergens) and the like.

In the present description, 'galactose' is a monosaccharide with 6 carbon atoms, and is aldose with an aldehyde group, and the chemical formula is $C_6H_{12}O_6$. Galactose and glucose are epimers with different stereochemical properties at carbon 4 (C4). The galactose used in the present description may be D-galactose, and may be in a monomer form which is not oligomerized and polymerized.

In the present description, 'treatment' may be used as a meaning that includes any reduction in the extent of disease, delay or alleviation of disease progression, alleviation, relief, stabilization, removal, partial or complete recovery of disease state or symptoms, prolongation of survival, other beneficial treatment results and the like. 'Prevention' may be used in a meaning that includes all mechanisms and/or effects that prevent the occurrence of a specific disease by acting on a subject that does not have the specific disease, or delay the time of its occurrence.

The subject of administration of the pharmaceutical composition or health functional food provided in the present description may be a mammal including humans, dogs, cats, horses, cows, pigs, goats, rabbits, mice, rats and the like, or a cell, tissue isolated therefrom, or its culture, and in one embodiment, the subject may be an individual (mammal such as humans and the like) which requires prevention or treatment of immune hypersensitivity-related disease described above (e.g., atopic dermatitis, allergic dermatitis, etc.) or has an immune hypersensitivity-related disease, or a cell, tissue isolated therefrom, or its culture thereof. The method of administration may be any conventional method, and for example, it may be oral administration, or parenteral administration such as transdermal administration (e.g., application to the skin), intravenous administration, intramuscular administration, subcutaneous administration, and intraperitoneal administration, and in particular, it may be administered by oral administration. The pharmaceutical composition may be used by formulation into oral formulations such as powders, granules, tablets, capsules, suspensions, emulsions, syrups, aerosols and the like according to a conventional method.

The pharmaceutical composition may be used by formulating into parenteral formulations in a form of transdermal agents, suppositories, and sterile injection solutions, oral formulations such as powders, granules, tablets, capsules, suspensions, emulsions, syrups, aerosols, and the like. In one embodiment, the pharmaceutical composition may be formulated for transdermal administration (transdermal agent), and for example, it may be formulated to be suitable for skin external application to the skin, such as an ointment, paste, cream, gel, emulsion (lotion), solution, suspension, powder, patch, form, spray, oil, or solid preparations, or the like.

The pharmaceutical composition provided in the present description may further contain an adjuvant such as a pharmaceutically appropriate and physiologically acceptable carrier, excipient, and/or diluent in addition to galactose as an active ingredient. The example of the carrier, excipient or diluent may include at least one selected from the group consisting of lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxy benzoate, propyl hydroxy benzoate, talc, magnesium stearate and mineral oil and the like. In the case of formulation, at least one diluent or excipient selected from the group consisting of commonly used fillers, extenders, binders, wetting agents, disintegrating agents, surfactants, and the like may be used. The solid preparation for oral administration may comprise at least one selected from the group consisting of tablets, pills, granules, capsules, syrup, powder, suspension and the like, and such a solid preparation may be prepared by mixing at least one excipient, for example, at least one selected from the group consisting of starch, calcium carbonate, sucrose, lactose, gelatin and the like, with galactose. In addition, lubricants such as magnesium stearate talc are used in addition to the simple excipient. At least one selected from the group consisting of suspensions, oral liquids, emulsions, syrups and the like correspond to liquid preparations for oral administration, and various excipients in addition to commonly used simple diluents, water and liquid paraffin, for example, at least one selected from the group consisting of wetting agents, sweeteners, flavoring agents, preservatives, and the like may be comprised.

Galactose as the pharmaceutical composition or active ingredient provided in the present description may be administered in a pharmaceutically effective dose. The dose of the galactose as the pharmaceutical composition or active ingredient may be prescribed in a variety of ways depending on factors such as formulation method, administration method, patient's age, body weight, gender, pathological condition, food, administration time, administration interval, excretion rate and response sensitivity. The dose may vary according to the patient's age, body weight, gender, administration form, state of health and degree of disease, and it may be divided into one or more doses taken at regular time intervals according to the judgement of a doctor or pharmacist. For example, the one-time or daily dose of the pharmaceutical composition may be in a range of 0.001 to 10000 mg/kg, specifically, 0.01 to 10000 mg/kg, 0.01 to 5000 mg/kg, 0.01 to 3000 mg/kg, 0.01 to 2500 mg/kg, 0.01 to 2000 mg/kg, 0.01 to 1500 mg/kg, 0.01 to 1000 mg/kg, 0.01 to 500 mg/kg, 0.01 to 300 mg/kg, 0.01 to 200 mg/kg, 0.1 to 10000 mg/kg, 0.1 to 5000 mg/kg, 0.1 to 3000 mg/kg, 0.1 to 2500 mg/kg, 0.1 to 2000 mg/kg, 0.1 to 1500 mg/kg, 0.1 to 1000 mg/kg, 0.1 to 500 mg/kg, 0.1 to 300 mg/kg, 0.1 to 200 mg/kg, 1 to 10000 mg/kg, 1 to 5000 mg/kg, 1 to 3000 mg/kg, 1 to 2500 mg/kg, 1 to 2000 mg/kg, 1 to 1500 mg/kg, 1 to 1000 mg/kg, 1 to 500 mg/kg, 1 to 300 mg/kg, 1 to 200 mg/kg, to 10000 mg/kg, 10 to 5000 mg/kg, 10 to 3000 mg/kg, 10 to 2500 mg/kg, 10 to 2000 mg/kg, 10 to 1500 mg/kg, 10 to 1000 mg/kg, 10 to 500 mg/kg, 10 to 300 mg/kg, to 200 mg/kg, 30 to 10000 mg/kg, 30 to 5000 mg/kg, 30 to 3000 mg/kg, 30 to 2500 mg/kg, 30 to 2000 mg/kg, 30 to 1500 mg/kg, 30 to 1000 mg/kg, 30 to 500 mg/kg, to 300 mg/kg, 30 to 200 mg/kg, 50 to 10000 mg/kg, 50 to 5000 mg/kg, 50 to 3000 mg/kg, 50 to 2500 mg/kg, 50 to 2000 mg/kg, 50 to 1500 mg/kg, 50 to 1000 mg/kg, to 500 mg/kg, 50 to 300 mg/kg, or 50 to 200 mg/kg, based on the active ingredient (galactose) weight, but not limited thereto. The single or daily dose may be formulated as a single unit dose form, or may be formulated in appropriate quantities, or may be prepared by placing it in a multi-dose container. The above dose is an example of an average case, and the dose may be higher or lower depending on individual differences.

The content of galactose contained in the pharmaceutical composition or health functional food provided in the present description is not particularly limited appropriately according to a form of a drug or food, a desired use, and the like, and for example, it may be 0.001 to 99% by weight, to 99% by weight, 0.01 to 95% by weight, 0.01 to 90% by weight, 0.01 to 80% by weight, 0.01 to 50% by weight, 0.1 to 99% by weight, 0.1 to 95% by weight, 0.1 to 90% by weight, 0.1 to 80% by weight, 0.1 to 50% by weight, 1 to 99% by weight, 1 to 95% by weight, 1 to 90% by weight, 1 to % by weight, 1 to 50% by weight, 10 to 99% by weight, 10 to 95% by weight, 10 to 90% by weight, 10 to 80% by weight, 10 to 50% by weight, 25 to 99% by weight, 25 to 95% by weight, 25 to 90% by weight, 25 to 80% by weight, 25 to 50% by weight, 40 to 99% by weight, 40 to 95% by weight, 40 to 90% by weight, 40 to 80% by weight, 40 to 50% by weight, 50 to 99% by weight, 50 to 95% by weight, 50 to 90% by weight, 50 to 80% by weight, 60 to 99% by weight, 60 to 95% by weight, 60 to 90% by weight, or 60 to 80% by weight of the total weight of the health functional food.

The health functional food is a food prepared using a nutrient that is easily deficient in daily meals or a raw material having functions beneficial to the human body (hereinafter referred to as 'functional raw material'), and means any food that helps to maintain health or prevent and/or alleviate (relieve) a certain disease or symptom, and there is no particular limitation on the final product form. For example, the health functional food may be selected from the group consisting of ordinary various types of foods, food supplements, beverages, food additives and the like, but not limited thereto. The health functional food may be in a solid, semi-solid or liquid form, and in particular may be formulated into powders, granules, tablets, capsules, suspensions, emulsions, syrups, aerosols and the like, but not limited thereto.

The health functional food may further contain at least one selected from the group consisting of various nutrients, vitamins, minerals (electrolytes), flavoring agents such as synthetic flavoring agents or natural flavoring agents, colorants, enhancers (cheese, chocolate, etc.), pectic acid or its salt, alginic acid or its salt, organic acids, protective colloidal thickeners, pH adjusting agents, stabilizers, preservatives, glycerin, alcohol, carbonating agents used for carbonated beverages. The ratio of such additive is generally selected from the range of 0.001 to about 20 parts by weight per 100 parts by weight of the total health functional food, but not limited thereto.

The cosmetic composition may be for prevention and/or alleviation of atopic syndrome (e.g., atopic dermatitis), allergic skin dermatitis, and the like.

The cosmetic composition may be prepared in a formulation selected from the group consisting of solutions, external ointment, cream, foam, nourishing cosmetic water, soft cosmetic water, packs, soft water, emulsion, make-up base, essence, soap, liquid cleansers, bath compositions, sunscreen cream, sun oil, suspension, emulsion, paste, gel, lotion, powders, soap, surfactant-containing cleansing, oil, powder foundation, emulsion foundation, wax foundation, patches, spray, and the like, but not limited thereto.

In addition, the cosmetic composition may further comprise at least one cosmetically acceptable carrier mixed to a general skin cosmetic, and for example, the carrier may be one which appropriately mixes at least one selected from the group consisting of oil, water, surfactants, moisturizers, lower alcohol, thickeners, chelating agents, pigments, preservatives, fragrance, and the like, but not limited thereto.

The cosmetically acceptable carrier comprised in the cosmetic composition may be appropriately selected according to the formulation. When the formulation is an ointment, paste, cream or gel, as a carrier component, animal oil, vegetable oil, wax, paraffin, starch, tragacanth, cellulose derivatives, polyethylene glycol, silicon, bentonite, silica, talc, zinc oxide, or a mixture thereof may be used. When the formulation is a powder or a spray, as a carrier component, lactose, talc, silica, aluminum hydroxide, calcium silicate, polyamide powder or a mixture of at least two of these may be used, and in particular, in case of a spray, it may additionally comprise a propellant such as chlorofluorohydrocarbone, propane/butane or dimethyl ether. When the formulation is solution or emulsion, as a carrier component, a solvent, a solubilizer and/or an emulsifier may be used, and for example, water, ethanol, isopropanol, ethyl carbonate, ethyl acetate, benzyl alcohol, benzyl benzoate, propylene glycol, 1,3-butylglycol oil, or a mixture of at least two thereof may be used, and in particular, cotton seed oil, peanut oil, corn germ oil, olive oil, castor oil and sesame oil, glycerol aliphatic ester, polyethylene glycol, fatty ester of sorbitan, or a mixture of at least two of these may be used. When the formulation is a suspension, as a carrier component, a liquid diluent such as water, ethanol or propylene glycol or the like, suspension such as ethoxylated isostearyl alcohol, polyoxyethylene sorbitol ester, and polyoxyethylene sorbitan ester and the like, microcrystalline cellulose, aluminum metahydroxide, bentonite, agar, tragacanth, or a mixture of at least two thereof may be used. When the formulation is a soap, as a carrier component, alkaline metal salts of fatty acids, fatty acid hemiester salts, fatty acid protein hydrolysate, isethionate, lanolin derivatives, aliphatic alcohol, vegetable oil, glycerol, sugar, or a mixture of at least two thereof may be used.

Advantageous Effects

As described above, the galactose provided in the present description has excellent effects of reducing spleen and lymph nodes, and reducing immunoglobulin E in the blood, and therefore, it can be effectively used for prevention, treatment and/or alleviation of various immune hypersensitivity-related diseases including atopic dermatitis.

BRIEF DESCRIPTION OF THE DRAWINGS

FIG. 1 shows the experimental animal preparation schedule in Reference example 1.

FIG. 2 is a photograph showing the appearance of lesions at the time of administration of a test drug in a DNCB-induced atopic dermatitis mouse model compared to a negative control group (PBS administration group; G3).

FIG. 3 is a graph showing the measurement result of ear thickness at the time of administration of a test drug in a DNCB-induced atopic dermatitis mouse model compared with a negative control group (PBS administration group; G3).

FIG. 4 is a graph showing the clinical scoring result at the time of administration of a test drug in a DNCB-induced atopic dermatitis mouse model compared to a negative control group (PBS administration group; G3).

FIG. 5 is a graph showing the spleen weight at the time of administration of a test drug in a DNCB-induced atopic dermatitis mouse model compared to a negative control group (PBS administration group; 3).

FIG. 6 is a graph showing the lymph node weight at the time of administration of a test drug in a DNCB-induced atopic dermatitis mouse model compared to a negative control group (PBS administration group; 3).

FIG. 7 is a graph showing the total amount of IgE in serum at the time of administration of a test drug in a DNCB-induced atopic dermatitis mouse model compared to a negative control group (PBS administration group; 3).

MODE FOR INVENTION

Hereinafter, the present invention will be described in more detail by the following examples. However, they are intended to illustrate the present invention only, but the scope of the present invention is not limited by these examples.

Reference Example 1. Preparation of Test Animals

An animal experiment in the following example was performed in accordance with the regulations set forth by Chonnam National University IACUC in an environment maintained at 50±5% humidity and 24~26° C. temperature. 7-week-old male BALB/c mice (Damool Science Co., Ltd.) bred as a test animal were used, and after being acclimatized in a laboratory environment for one week while supplying enough feed and water, they were used in the experiment. Non-allergenic, dust-free, non-toxic, absorbent and pathogen-free bedding was used, and the cage was changed once a week to maintain a clean environment, and water was freely supplied with a water bottle.

Galactose was pre-administered for 2 weeks from the period when the prepared mice were 8-week-old. Pre-administration was performed by oral administration once a day for 2 weeks, and the dose of galactose was 100 mg/kg or 200 mg/kg, respectively. As a control group, mice administered (orally) with PBS for the same period were prepared. After 2 weeks of pre-administration, the hairs on the mouse head and back of the mice were removed using a clipper and depilatory cream.

To induce atopic dermatitis, 2,4-Dinitrochlorobenzene (hereinafter, DNCB'; Sigma-aldrich) was dissolved in a solvent (acetone:olive oil=3:1 (v:v)) and used. The concentration of the DNCB was used at 1.5% (w/v) for Sensitization and used at 0.4% (w/v) for Challenge. Atopic dermatitis was induced by applying 200 ul, and 50 ul of the DNCB solution at the above concentration to the mouse back and ear of the mice twice a week, respectively. A total of 2 Sensitizations and 3 Challenges were performed. Through this, a DNCB-induced atopic dermatitis mouse model was prepared.

Galactose was administered orally at 100 mg/kg or 200 mg/kg daily for 16 days from the first DNCB application (Day 0). For comparison, a negative control group administered with PBS instead of galactose to the atopic dermatitis-induced mice and a positive control group intraperitoneally administered with dexamethasone 5 mg/kg from the first DNCB application (Day 0) were prepared. On the day 16 after the first DNCB application (just before necropsy), ear thickness and clinical symptoms of the mice were measured.

The prepared experimental animals were summarized in Table 1 below:

TABLE 1

| Group | Classification | Administration method | Test drug | Concentration (per 1 time) | Number (animals) |
|---|---|---|---|---|---|
| G1 | Vehicle treat (control) | Oral administration | PBS | — | 7 |
| G2 | Vehicle treat | Oral administration | galactose (Galactose; G) | 200 mg/kg | 7 |
| G3 | Atopic dermatitis + Negative control | Oral administration | PBS | — | 7 |
| G4 | Atopic dermatitis + Positive control | Intraperitoneal administration | Dexamethasone (Dex) | 5 mg/kg | 7 |
| G5 | Atopic dermatitis + Middle dose | Oral administration | galactose | 100 mg/kg | 7 |
| G6 | Atopic dermatitis + High dose | Oral administration | galactose | 200 mg/kg | 7 |
| | | Sum | | | 42 |

Reference Example 2. Experimental Method (1) Clinical Scoring & Ear Thickness Evaluation The mice prepared in Reference example 1 were evaluated for clinical symptoms (rubefaction, keratin formation (dryness degree), crust formation), and ear thickness was measured and then recorded three times a week (Monday, Wednesday, Friday). Ear thickness was measured three times a week using Caliper (R12-1A, Ozaki, Tokyo, Japan).

(2) Blood Analysis

At autopsy (16 days after first DNCB application), whole blood was collected, and then serum was separated and the IgE level in serum was measured by ELISA.

(3) Histopathological Analysis

At autopsy, the skin tissue and ear were fixed in formalin, and the fixed tissue was used to prepare paraffin embedding, and through H&E staining and Toluidine blue staining, Mast cells were stained. In addition, histological observation was performed through an optical microscope.

Example 1. Visual Confirmation of Atopic Dermatitis

On the day before autopsy of the mice prepared in Reference example 1, in order to confirm the overall atopic reaction of the mice, a picture was taken of the area where DNCB was applied (atopic dermatitis-induced area).

The obtained result was shown in FIG. 2 (n=2 per each group). As shown in FIG. 2, skin inflammatory lesions such as skin rubefaction, keratin formation, crust formation and the like in the DNCB-treated mice (G3, G4, G5, G6) were observed, and among the DNCB-treated groups, compared to the negative control group (G3), in the groups orally administered with galactose (G) (G5, G6), the degree of skin rubefaction was suppressed and the degree of crust formation was reduced.

Example 2. Measurement of Mouse Ear Thickness

As the ear thickness increases due to inflammatory symptoms such as edema and rubefaction and the like when DNCB is treated in the DNCB-induced atopic dermatitis mouse model, in the present example, by measuring the ear thickness, the degree of symptoms of atopic dermatitis can be evaluated indirectly (the thicker the ear thickness is, the more severe the symptoms of atopic dermatitis are).

Referring to (1) of Reference example 2, the ear thickness of the mice prepared in Reference example 1 was measured, and the result was shown in FIG. 3. As shown in FIG. 3, it was observed that the ear thickness increased in the DNCB-treated mouse group compared to the untreated group, and it could be confirmed that the ear thickness was significantly reduced in the groups administered with galactose (G5, G6).

Example 3. Evaluation of Clinical Symptoms of Atopic Dermatitis

As it was known that skin inflammatory symptoms such as rubefaction, keratin formation, crust formation, and the like as clinical symptoms of atopic dermatitis were increased when DNCB was treated to skin in the DNCB-induced atopic dermatitis mouse model, in the present example, by evaluating rubefaction, keratin formation, and crust formation of the DNCB-applied area as clinical symptoms, a protective effect of atopic dermatitis was indirectly evaluated.

For the mice prepared in Reference example 1, the clinical symptoms of the three items (rubefaction, keratin formation (dryness), crust formation) were scored on the basis of the following: 0 point; none, 1 point; mild, 2 points; moderate, 3 points; severe.

The obtained result (Clinical scoring; sum of the scores of the three items) was shown in FIG. 4. As shown in FIG. 4, it could be confirmed that in the DNCB-treated mouse group, compared to the non-treated group, the score of clinical symptoms of skin was increased, and compared to the negative control group (G3), in the galactose administration groups (G5, G6), the score of clinical symptoms was significantly reduced.

Example 4. Measurement of Spleen and Lymph Node Weight

It was known that the spleen and lymph nodes, which are immune organs, were enlarged, when DNCB was treated to skin in the DNCB-induced atopic dermatitis mouse model. In the present example, by measuring the weight of the spleen and armpit lymph nodes right before autopsy of the mice prepared in Reference example 1, a protective effect of atopic dermatitis was indirectly evaluated.

The obtained result was shown in FIG. 5 (spleen weight) and FIG. 6 (lymph node weight). As shown in FIG. 5 and FIG. 6, it could be confirmed that the weight of spleen and lymph nodes was increased in the DNCB-treated mouse group compared to the non-treated group, and the weight of spleen and lymph nodes was generally reduced in the galactose administration groups (G5, G6), compared to the negative control group (G3).

Example 5. Total Amount of Immunoglobulin E (IgE) in Mouse Serum

As total IgE in serum was increased, when DNCB was treated to skin in the DNCB-induced atopic dermatitis mouse model, in the present example, by collecting blood right before autopsy of the mice prepared in Reference example 1 and then isolating serum and evaluating the total amount of IgE (ug/ml) in serum through ELISA method, a protective effect of atopic dermatitis was indirectly evaluated.

The obtained result was shown in FIG. 7. As shown in FIG. 7, it could be confirmed that the numerical value of IgE in serum was increased in the DNCB-treated mouse group, compared to the non-treated group, and the total amount of IgE was significantly reduced in the galactose administration group (G6) compared to the negative control group (G3).

As described above, oral administration of galactose in the atopy-induced mouse model was evaluated to induce alleviation of atopic symptoms in the indicators such as clinical symptoms (rubefaction, keratin formation, crust formation, etc.) and change in ear thickness, visual findings on skin, lymph node size and serum IgE level and the like.

The invention claimed is:

1. A method for treatment or alleviation of immune hypersensitivity-related disease, comprising administering effective amount of a composition consisting of (1) galactose, or (2) galactose and one or more pharmaceutically acceptable or cosmetically acceptable carriers, excipients or diluents selected from the group consisting of fillers, extenders, binders, wetting agents, disintegrating agents, surfactants, sweeteners, flavoring agents, preservatives, oils, water, surfactants, moisturizers, lower alcohols, thickeners, chelating agents, pigments, preservatives, fragrances, emulsifiers, propellants and solvents, to a subject in need of treatment or alleviation of the immune hypersensitivity-related disease, wherein immune hypersensitivity-related disease is atopic syndrome or atopic dermatitis.

2. The method for treatment or alleviation of immune hypersensitivity-related disease according to claim 1, further comprising identifying the subject in need of treatment or alleviation of immune hypersensitivity-related disease prior to the administration.

3. A method of reducing immunoglobulin E, comprising administering a pharmaceutically effective amount of a composition consisting of (1) galactose, or (2) galactose and one or more pharmaceutically acceptable or cosmetically acceptable carriers, excipients or diluents selected from the group consisting of fillers, extenders, binders, wetting agents, disintegrating agents, surfactants, sweeteners, flavoring agents, preservatives, oils, water, surfactants, moisturizers, lower alcohols, thickeners, chelating agents, pigments, preservatives, fragrances, emulsifiers, propel-lants and solvents, to a subject in need of reducing immunoglobulin E.

4. The method of reducing immunoglobulin E according to claim 3, further comprising identifying the subject in need of reducing immunoglobulin E, before the administering.

* * * * *